(12) United States Patent
Sato

(10) Patent No.: US 11,241,217 B2
(45) Date of Patent: Feb. 8, 2022

(54) ULTRASOUND PROBE AND ULTRASOUND ENDOSCOPE

(71) Applicant: OLYMPUS CORPORATION, Tokyo (JP)

(72) Inventor: Sunao Sato, Yamato (JP)

(73) Assignee: OLYMPUS CORPORATION, Tokyo (JP)

(*) Notice: Subject to any disclaimer, the term of this patent is extended or adjusted under 35 U.S.C. 154(b) by 340 days.

(21) Appl. No.: 16/248,956

(22) Filed: Jan. 16, 2019

(65) Prior Publication Data
US 2019/0142376 A1    May 16, 2019

Related U.S. Application Data

(63) Continuation of application No. PCT/JP2017/011836, filed on Mar. 23, 2017.

(30) Foreign Application Priority Data

Jul. 19, 2016    (JP) .............................. JP2016-141615

(51) Int. Cl.
*A61B 8/00*    (2006.01)
*A61B 8/12*    (2006.01)
*A61B 8/14*    (2006.01)

(52) U.S. Cl.
CPC ................ *A61B 8/445* (2013.01); *A61B 8/12* (2013.01); *A61B 8/14* (2013.01); *A61B 8/546* (2013.01)

(58) Field of Classification Search
None
See application file for complete search history.

(56) References Cited

U.S. PATENT DOCUMENTS 5,721,463 A * 2/1998 Snyder ................... A61B 8/546
                                                      310/327
2008/0009742 A1 * 1/2008 Kondoh ............. G01N 29/2437
                                                      600/459

(Continued)

FOREIGN PATENT DOCUMENTS

CN    101219062 A    7/2008
CN    101361664 A    2/2009

(Continued)

OTHER PUBLICATIONS

International Search Report dated Jun. 20, 2017 issued in PCT/JP2017/011836.

*Primary Examiner* — Bill Thomson
*Assistant Examiner* — Younhee Choi
(74) *Attorney, Agent, or Firm* — Scully, Scott, Murphy & Presser, P.C.

(57) ABSTRACT

An ultrasound probe includes: a casing; a plurality of piezoelectric devices that are arranged inside the casing; an acoustic matching layer that is attached to ultrasound radiation surfaces of the piezoelectric devices; a shared ground that is arranged on a surface of the acoustic matching layer to allow at least a part of the shared ground to come in contact with the piezoelectric devices; a deformation preventing member that is arranged in contact with the surface of the acoustic matching layer to surround an outer periphery of the piezoelectric devices and to be separated from the piezoelectric devices; a coaxial line configured to transmit a signal to each of the piezoelectric devices; and a circuit board that is arranged on an opposite side to the ultrasound radiation surfaces of the piezoelectric devices, the circuit board being configured to electrically connect the piezoelectric devices and the coaxial line.

8 Claims, 8 Drawing Sheets

(56) References Cited

U.S. PATENT DOCUMENTS

| | | | |
|---|---|---|---|
| 2008/0051655 A1 | 2/2008 | Sato et al. | |
| 2008/0077017 A1* | 3/2008 | Hyuga | A61B 8/12 600/459 |
| 2008/0312537 A1* | 12/2008 | Hyuga | B06B 1/0622 600/459 |
| 2009/0010459 A1* | 1/2009 | Garbini | B06B 1/0622 381/190 |
| 2009/0034370 A1 | 2/2009 | Guo | |
| 2012/0143060 A1* | 6/2012 | Weekamp | G10K 11/004 600/459 |
| 2013/0145611 A1* | 6/2013 | Guo | H04R 31/00 29/594 |
| 2015/0245815 A1* | 9/2015 | Wakabayashi | H01L 41/29 367/140 |

FOREIGN PATENT DOCUMENTS

| | | |
|---|---|---|
| JP | 2001-327494 A | 11/2001 |
| JP | 2008-079700 A | 4/2008 |
| JP | 2011-229976 A | 11/2011 |

* cited by examiner

ULTRASOUND PROBE AND ULTRASOUND ENDOSCOPE

CROSS-REFERENCE TO RELATED APPLICATION

This application is a continuation of PCT International Application No. PCT/JP2017/011836 filed on Mar. 23, 2017 which claims the benefit of priority from Japanese Patent Application No. 2016-141615, filed on Jul. 19, 2016, the entire contents of which are incorporated herein by reference.

BACKGROUND

1. Technical Field

The present disclosure relates to an ultrasound probe and an ultrasound endoscope.

2. Related Art

In the related art, ultrasound probes that transmit ultrasonic waves to an object to be observed, that receives an ultrasound echo reflected by the object to be observed and converts it into an electrical signal, and that subjects the signal to a predetermined signal process, to acquire information relating to characteristics of the object to be observed have been known.

The ultrasound probe includes plural piezoelectric devices that convert an electrical pulse signal into an ultrasonic pulse (acoustic pulse) to irradiate it to an object to be observed, and that converts an ultrasound echo reflected by the object to be observed into an electrical echo signal to output. For example, the piezoelectric devices are aligned along a predetermined direction, and devices involved in transmission and reception are switched thereamong, thereby acquiring ultrasound echo from the object to be observed.

Moreover, the ultrasound probe includes an acoustic matching layer that is attached to an ultrasound radiation surface of the piezoelectric devices, an acoustic lens that forms an external surface of the ultrasound probe, a backing material that is arranged on a surface of the piezoelectric devices on an opposite side to the acoustic matching layer, and the like.

When the ultrasound probe is actuated, the piezoelectric devices can generate heat. Moreover, part of ultrasonic waves transmitted from the piezoelectric device can converted into heat at the acoustic matching layer, the backing material, the acoustic lens, and the like, and the inside of the ultrasound probe can be heated.

Japanese Laid-open Patent Publication No. 2011-229976 discloses an ultrasound probe that includes a heat radiation member radiating heat inside the ultrasound probe to bring the temperature of a portion contacting a tissue of the ultrasound probe to equal to or lower than a threshold.

SUMMARY

In some embodiments, an ultrasound probe includes: a casing; a plurality of piezoelectric devices that are arranged inside the casing; an acoustic matching layer that is attached to ultrasound radiation surfaces of the piezoelectric devices; a shared ground that is arranged on a surface of the acoustic matching layer, on a side on which the acoustic matching layer is in contact with the piezoelectric devices, to allow at least a part of the shared ground to come in contact with the piezoelectric devices; a deformation preventing member that is arranged in contact with the surface of the acoustic matching layer to surround an outer periphery of the piezoelectric devices and to be separated from the piezoelectric devices; a coaxial line configured to transmit a signal to each of the piezoelectric devices; and a circuit board that is arranged on an opposite side to the ultrasound radiation surfaces of the piezoelectric devices, the circuit board being configured to electrically connect the piezoelectric devices and the coaxial line.

In some embodiments, an ultrasound endoscope includes: an imaging optical system to image a subject; a casing; a plurality of piezoelectric devices that are arranged inside the casing; an acoustic matching layer that is attached to ultrasound radiation surfaces of the piezoelectric devices; a shared ground that is arranged on a surface of the acoustic matching layer, on a side on which the acoustic matching layer is in contact with the piezoelectric devices, to allow at least a part of the shared ground to come contact with the piezoelectric devices; a deformation preventing member that is arranged in contact with the surface of the acoustic matching layer to surround an outer periphery of the piezoelectric devices and to be separated from the piezoelectric devices; a coaxial line configured to transmit a signal to each of the piezoelectric devices; and a circuit board that is arranged on an opposite side to the ultrasound radiation surfaces of the piezoelectric devices, the circuit board being configured to electrically connect the piezoelectric devices and the coaxial line.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasound probe according to the disclosure are explained below with reference to the drawings. These embodiments are not intended to limit the disclosure. In the following embodiments, a convex ultrasound probe is explained by way of example, but the disclosure is applicable to common ultrasound probes including linear and radial ultrasound probes.

Moreover, like reference symbols are appropriately assigned to like components or corresponding components throughout the drawings. Furthermore, it should be noted that the drawings illustrate schematic forms, and relationship in dimensions among the components, the ratio among the components, and the like can differ from an actual situation. Among the drawings also, inconsistency in the relationship in dimensions or in the ratio can be included.

First Embodiment

Figure 1:
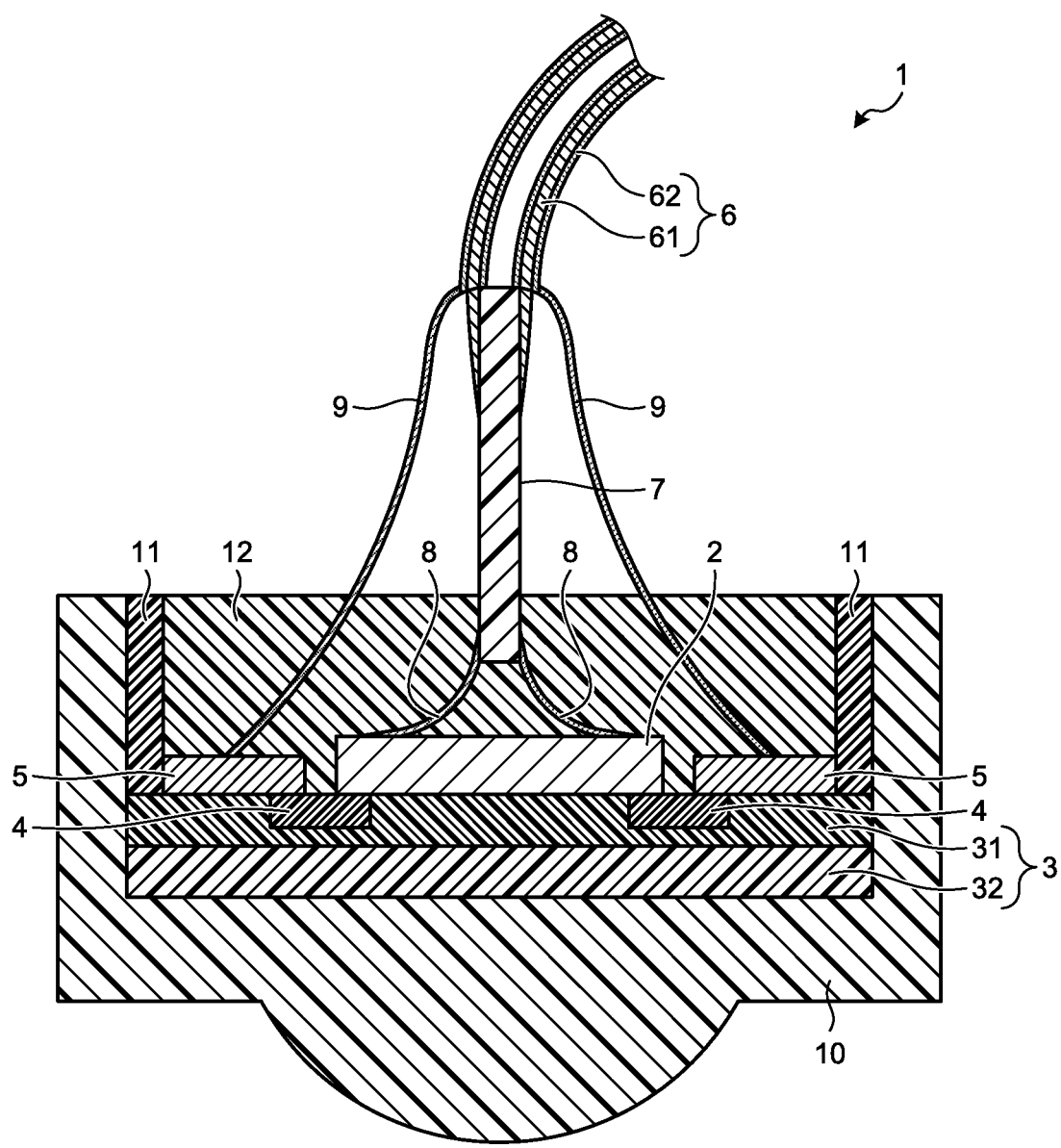
FIG. 1 is a cross-section of an ultrasound probe according to a first embodiment of the disclosure.

FIG. 1 is a cross-section of an ultrasound probe according to a first embodiment of the disclosure. As shown in FIG. 1, an ultrasound probe 1 according to the first embodiment includes plural piezoelectric devices 2, an acoustic matching layer 3 that is attached to ultrasound radiation surfaces (surface of the piezoelectric device 2 positioned at a lower portion on a sheet of FIG. 1) of the piezoelectric devices 2, a shared ground 4 that is arranged on a surface of the acoustic matching layer 3 on a side on which the acoustic matching layer 3 is in contact with the piezoelectric devices 2 (surface of the acoustic matching layer 3 positioned at an upper portion on the sheet of FIG. 1) so as to be in contact with the piezoelectric devices 2, a heat radiation plate 5 serving as a deformation preventing member that is arranged in contact with the surface of the acoustic matching layer 3 on the side on which the acoustic matching layer 3 is in contact with the piezoelectric devices 2, plural coaxial lines 6 that transmit a signal to the respective piezoelectric devices 2, a circuit board 7 that is arranged on an opposite side to the ultrasound radiation surfaces of the piezoelectric devices 2, and that electrically connects the piezoelectric devices 2 and the coaxial lines 6, a wire 8 that electrically connects the piezoelectric devices 2 and the circuit board 7, a heat conduction path 9 that transfers heat of the heat radiation plate 5 to the coaxial lines 6, an acoustic lens 10 that is arranged on an opposite side to the surface of the acoustic matching layer 3 on the side on which the acoustic matching layer 3 is in contact with the piezoelectric devices 2, a casing 11 that is arranged uprightly on the surface of the acoustic matching layer 3 on a side on which the acoustic matching layer 3 is in contact with the piezoelectric devices 2, and a backing material that is arranged on an opposite side to the ultrasound radiation surfaces of the piezoelectric devices 2.

Figure 2:
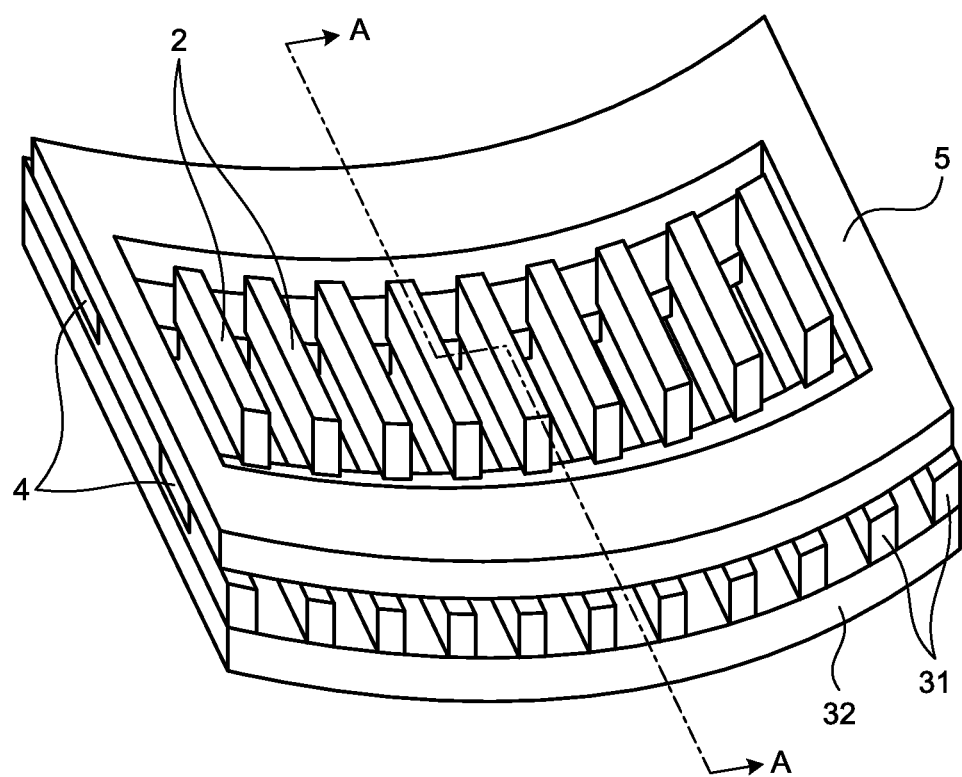
FIG. 2 is a perspective view showing part of the ultrasound probe shown in FIG. 1.

FIG. 2 is a perspective view showing part of the ultrasound probe shown in FIG. 1. The cross-section taken along a line A-A in FIG. 2 corresponds to FIG. 1. As shown in FIG. 2, the piezoelectric devices 2 are aligned to be apart from one another. To each piezoelectric device 2, the wire 8 (not shown in FIG. 2) shown in FIG. 1 is connected. Each of the piezoelectric devices 2 converts an electrical pulse signal to an acoustic pulse to irradiate to a subject, and converts an ultrasonic echo reflected by the subject into an electrical echo signal that is expressed by voltage change to output.

The acoustic matching layer 3 includes first acoustic-matching layers 31, each of which is arranged in contact with the piezoelectric device 2, and a plate-shaped second acoustic-matching layer 32 that is in contact with the respective first acoustic matching layers 31. The first acoustic-matching layers 31 and the second acoustic-matching layer 32 match an acoustic impedance of the piezoelectric devices 2 and an acoustic impedance of an object to be observed, for efficient transmission of sound (ultrasound) between the piezoelectric devices 2 and the object to be observed. The first acoustic-matching layers 31 and the second acoustic-matching layer 32 are made from various kinds of synthetic resins, such as epoxy resin, and are made from different materials from each other. In the first embodiment, explanation is given assuming that two kinds of acoustic matching layers (the first acoustic-matching layers 31 and the second acoustic-matching layer 32) are provided, but the acoustic matching layer can be of one layer, or three or more layers depending on characteristics of the piezoelectric device 2 and an object to be observed.

The shared ground 4 is made from an electric conductive resin, is in a continuous form along a direction of alignment of the piezoelectric devices 2, and is in contact with the piezoelectric devices 2, the first acoustic-matching layers 31, and the heat radiation plate 5. The continuous-formed shared ground 4 can be obtained by filling resin, after layers corresponding to the first acoustic-matching layer 31, a shared ground 4, and the piezoelectric devices 2 in a laminated body including the second acoustic-matching layer 32, the first acoustic-matching layer 31, the shared ground 4, and the piezoelectric devices 2 are cut to be separated in the direction of alignment of the piezoelectric devices 2, and are bent into a predetermined shape, such that only the shared ground 4 becomes a non-separated form. It is also applicable that layers corresponding to the first acoustic-matching layer 31 and the piezoelectric devices 2 in a laminated body including the second acoustic-matching layer 32, the first acoustic-matching layer 31, and the piezoelectric devices 2 are cut, resin is filled to form a continuous-formed shared ground 4, and it is thereafter bent into a predetermined shape. Furthermore, the shared ground 4 is grounded to the outside through the heat radiation plate 5, the heat conduction path 9, and the coaxial lines 6.

The heat radiation plate 5 is arranged to surround an outer periphery of the piezoelectric device 2, being separated from the piezoelectric device 2. Moreover, the heat radiation plate 5 is made from an electric conductive material. Specifically, the heat radiation plate 5 is made from metal having superior electric conductivity, heat conductivity, and rigidity, and is arranged in contact with the shared ground 4 and the first acoustic-matching layer 31. Furthermore, the acoustic matching layer 3 and the heat radiation plate 5 are curved at the same curvature. Moreover, to the heat radiation plate 5, the heat conduction path 9 is connected as shown in FIG. 1.

The coaxial line 6 includes a signal line 61 that transmits a signal to each of the piezoelectric devices 2, and an external conductor 62 that is arranged on an outer periphery of the signal line 61. In other words, the coaxial lines 6 in the same quantity as the piezoelectric devices 2 are connected to the piezoelectric devices 2, respectively. The signal line 61 and the external conductor 62 are electrically insulated.

The circuit board 7 is a printed board including electrical wirings on both sides in a left and right directions on the sheet of FIG. 1, and each of the signal lines 61 is soldered to one end (upper end in FIG. 1) of the circuit board 7, and the wire 8 is soldered to the other end (lower end in FIG. 1) of the circuit board 7. As a result, the respective piezoelectric devices 2 and the respective signal lines 61 are electrically connected.

The heat conduction path 9 is connected to the heat radiation plate 5 and the external conductor 62, and transmits heat of the heat radiation plate 5 to the external conductor 62. The number of the heat conduction path 9 is not particularly limited but, for example, two each of the heat conduction paths 9 are connected to each of the external conductor 62.

The acoustic lens 10 covers the first acoustic-matching layer 31, the second acoustic-matching layer 32, and the casing 11. The acoustic lens 10 forms an external surface of the ultrasound probe 1. The acoustic lens 10 is formed by using silicone, polyethylpentene, epoxy resin, polyetherimide, or the like, has a convex or concave shape on one side to have a function of reducing ultrasonic waves, and emits ultrasonic waves that have passed through the second acoustic-matching layer 32 to the outside or takes in an ultrasound echo from the outside. The acoustic lens 10 can be arranged arbitrarily, and a structure without the acoustic lens 10 is also applicable.

The backing material 12 is formed by using hard resin, and is filled in space surrounded by the casing 11.

The ultrasound probe 1 having the above structure irradiates ultrasonic waves to an object to be observed through the first acoustic-matching layer 31, the second acoustic-matching layer 32, and the acoustic lens 10 by an vibration of the piezoelectric devices 2 due to an input of a pulse signal. At this time, in the piezoelectric device 2, on the opposite side to a side on which the first acoustic-matching layer 31, the second acoustic-matching layer 32, and the acoustic lens 10 are arranged, the backing material 12 attenuates unnecessary ultrasonic vibrations from the piezoelectric devices 2. Moreover, an ultrasound echo reflected from the object to be observed is transferred to the piezoelectric devices 2 through the acoustic lens 10, the second acoustic-matching layer 32, and the first acoustic-matching layer 31. The piezoelectric devices 2 are caused to vibrate by the transferred ultrasound echo, and the piezoelectric devices 2 convert the vibrations into an electrical echo signal to output to an ultrasound observation device not shown through the signal line 61 as an echo signal.

In the ultrasound probe 1, heat inside the ultrasound probe 1 is transferred sequentially to the piezoelectric devices 2, the shared ground 4, the heat radiation plate 5, the heat conduction path 9, and then the external conductor 62 by the heat radiation plate 5 made from metal, to be radiated to the outside. Furthermore, in the ultrasound probe 1, the heat radiation plate 5 is arranged in contact with the first acoustic-matching layer 31, thereby preventing deformation of the first acoustic-matching layer 31. Furthermore, the heat radiation plate 5 also prevents deformation of the second acoustic-matching layer 32 through the first acoustic-matching layer 31. Therefore, the ultrasound probe 1 according to the first embodiment is an ultrasound probe enabling to prevent deterioration of performance of the ultrasound probe due to heat.

First Modification

Figure 3:
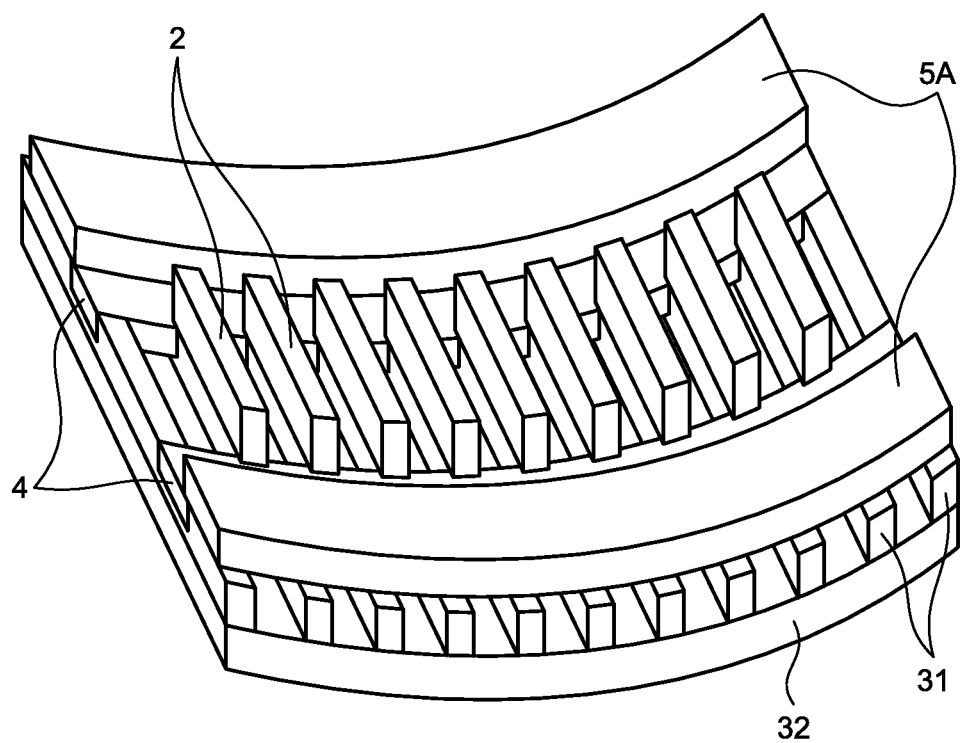
FIG. 3 is a perspective view showing part of an ultrasound probe according to a first modification of the first embodiment.

FIG. 3 is a perspective view showing part of an ultrasound probe according to a first modification of the first embodiment. As shown in FIG. 3, the ultrasound probe 1 according to the first modification of the first embodiment includes two heat radiation plates 5A that extend along the direction of alignment of the piezoelectric devices 2. To the heat radiation plates 5A, the heat conduction paths 9 not shown are respectively connected. As described, a form of the heat radiation plate is not limited.

Second Modification

Figure 4:
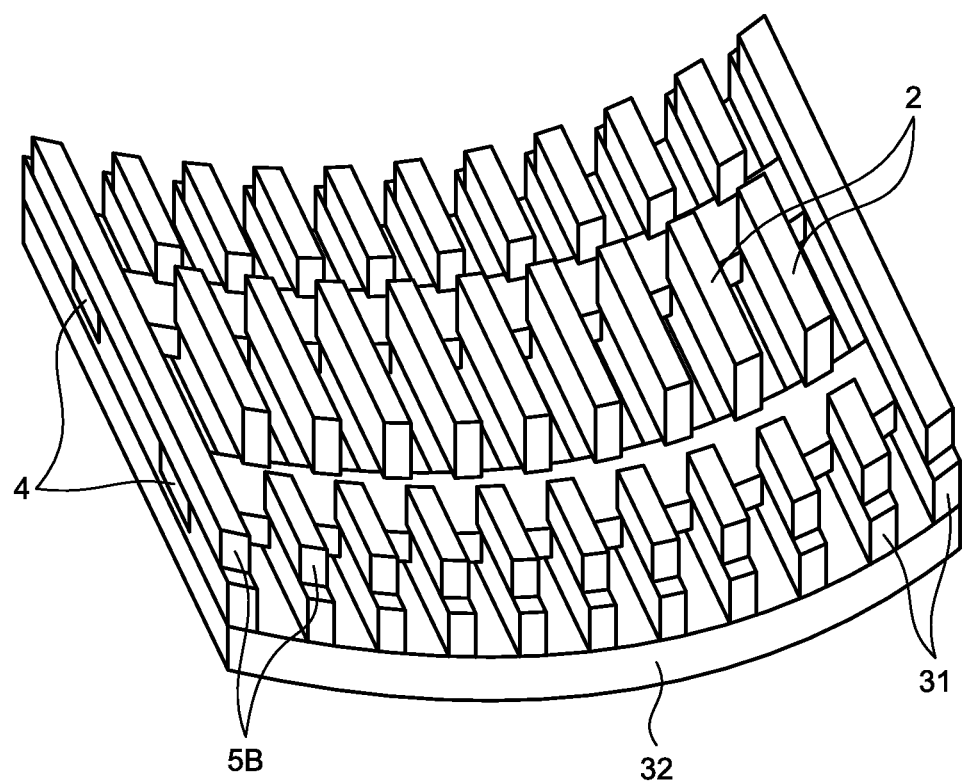
FIG. 4 is a perspective view showing part of an ultrasound probe according to a second modification of the first embodiment.

FIG. 4 is a perspective view showing part of an ultrasound probe according to a second modification of the first embodiment. As shown in FIG. 4, the ultrasound probe 1 according to the second modification of the first embodiment includes plural heat radiation plates 5B that are arranged to be in contact with the respective first acoustic-matching layers 31 in one to one correspondence, separated one another. To the heat radiation plates 5B, the heat conduction paths 9 not shown are respectively connected. In the second modification, heat inside the ultrasound probe 1 is sufficiently radiated by the heat radiation plates 5B. As a result, in the second modification, increase of temperature inside the ultrasound probe 1 is suppressed by the heat radiation plates 5B, thereby preventing deformation of the first acoustic-matching layer 31.

Third Modification

Figure 5:
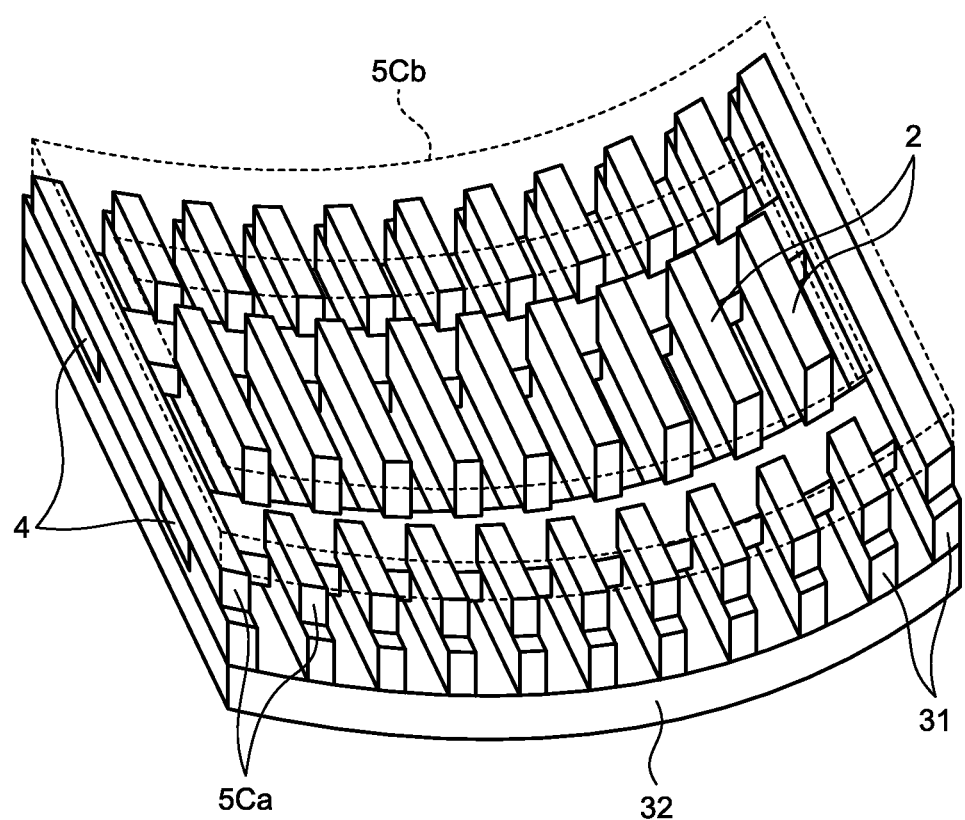
FIG. 5 is a perspective view showing part of an ultrasound probe according to a third modification of the first embodiment.

FIG. 5 is a perspective view showing part of an ultrasound probe according to a third modification of the first embodiment. As shown in FIG. 5, the ultrasound probe 1 according to the third modification of the first embodiment includes plural heat radiation plates 5C$a$ that are arranged to be in contact with the respective first acoustic-matching layers 31 in one to one correspondence, separated one another, and a rigid member 5C$b$ that has a continuous form along the direction of alignment of the piezoelectric devices 2. In FIG. 5, the rigid member 5C$b$ is illustrated by a broken line so that the heat radiation plates 5C$a$ are more recognizable. To the heat radiation plates 5C$a$, the heat conduction paths 9 not shown are respectively connected. In the third modification, heat inside the ultrasound probe 1 is radiated by the heat radiation plates 5C$a$. Furthermore, in the third modification, the rigid member 5C$b$ prevents deformation of the first acoustic-matching layer 31 and the second acoustic-matching layer 32 through the heat radiation plates 5C$a$.

Fourth Modification

Figure 6:
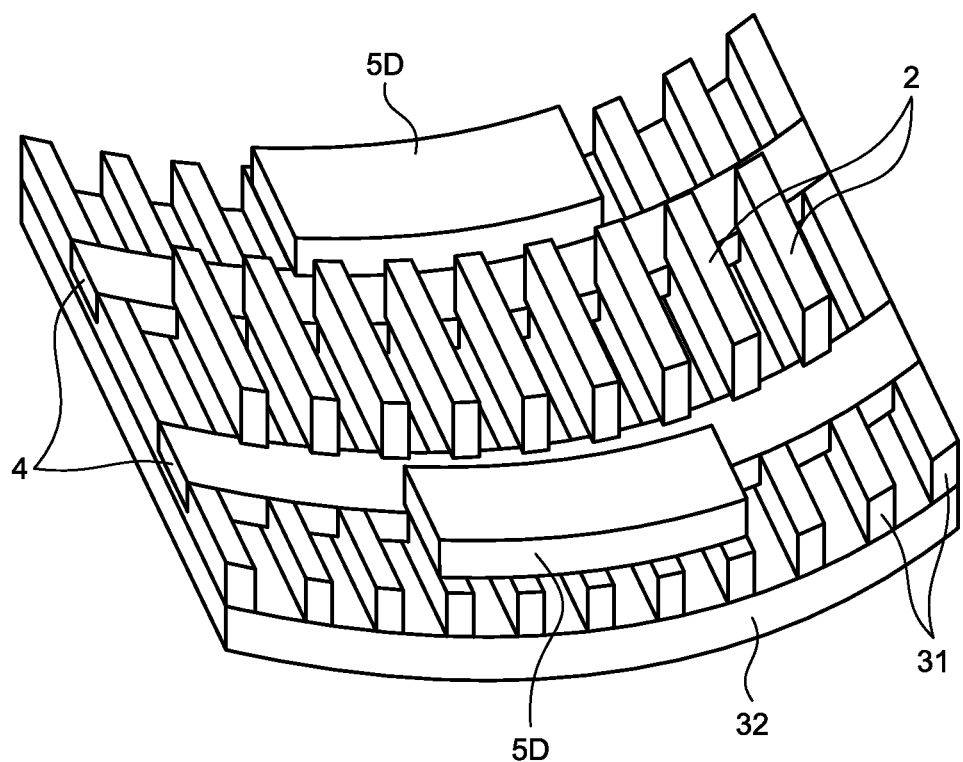
FIG. 6 is a perspective view showing part of an ultrasound probe according to a fourth modification of the first embodiment.

FIG. 6 is a perspective view showing part of an ultrasound probe according to a fourth modification of the first embodiment. As shown in FIG. 6, the ultrasound probe 1 according to the fourth modification of the first embodiment includes two heat radiation plates 5D in a continuous form that are arranged in a central portion. To the respective heat radiation plates 5D, the heat conduction paths 9 not shown are respectively connected. In the fourth modification, heat inside the ultrasound probe 1 is radiated by the heat radiation plates 5D, and deformation of the first acoustic-matching layer 31 and the second acoustic-matching layer 32 are prevented. As a result, according to the fourth modification, it is possible to prevent deformation of a central portion of the first acoustic-matching layer 31, which is important during observation, and to reduce manufacturing costs because it has a simpler structure than that in the first embodiment. The structure in which the heat radiation plates are arranged in a central portion selectively is also applicable to a linear ultrasound probe.

Second Embodiment

Figure 7:
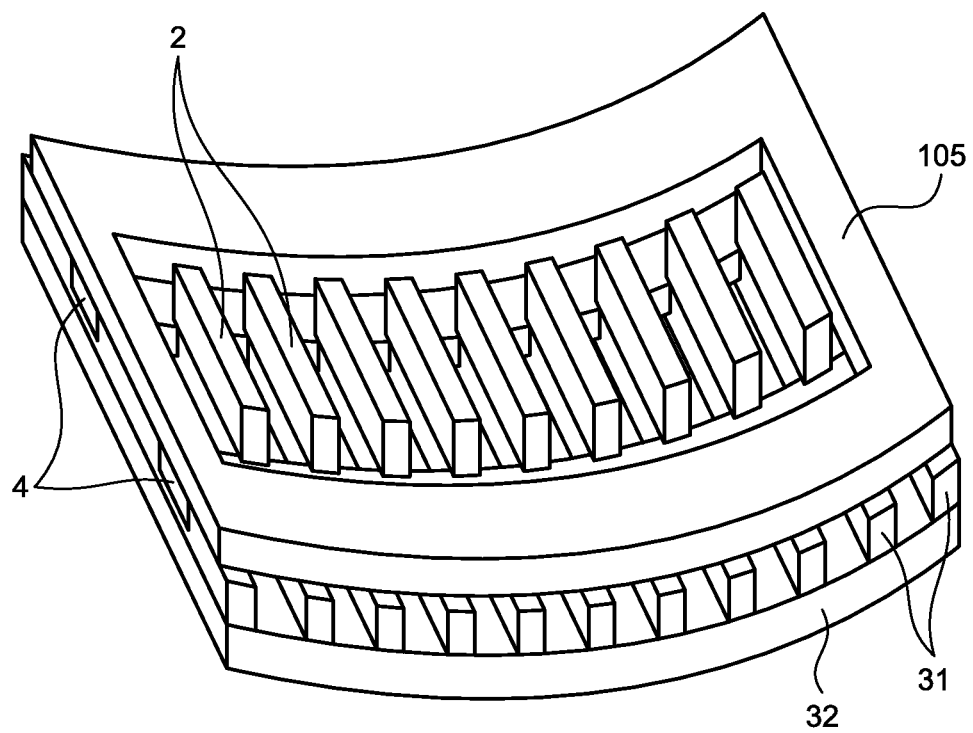
FIG. 7 is a perspective view showing part of an ultrasound probe according to a second embodiment.

FIG. 7 is a perspective view showing part of an ultrasound probe according to a second embodiment. As shown in FIG. 7, the ultrasound probe 1 according to the second embodiment includes a heat radiation plate 105 serving as a deformation preventing member that is arranged on a surface of the acoustic matching layer 3 (the first acoustic-matching layer 31) on a side on which the acoustic matching layer 3 is in contact with the piezoelectric devices 2, in contact with the acoustic matching layer 3 (the first acoustic-matching layer 31), similarly to the first embodiment.

Because other components can be the same as the first embodiment, explanation is omitted appropriately.

The heat radiation plate 105 is made from an electric conductive shape-memory alloy, such as Ni—Ti. The temperature at which a shape-memory alloy returns to the original shape (transformation point) can be controlled to a desired temperature by adjusting the amount of Ni. The heat radiation plate 105 is set to have the transformation point to 40° C. to 50° C., and the transformation point is included in a temperature range assumed at a use, heat processing, cleaning, and the like of the endoscope. When the heat radiation plate 105 reaches a temperature equal to or higher than the transformation point, the heat radiation plate 105 transforms to a curved shape having the same curvature as the acoustic matching layer 3 that has not been deformed (the original shape).

According to the second embodiment, when the temperature inside the ultrasound probe 1 becomes high temperature that is a temperature equal to or higher than a transformation point, the heat radiation plate 105 in contact with the first acoustic-matching layer 31 returns to the original shape and, therefore, deformation of the first acoustic-matching layer 31 and the second acoustic-matching layer 32 are prevented.

Third Embodiment

Figure 8:
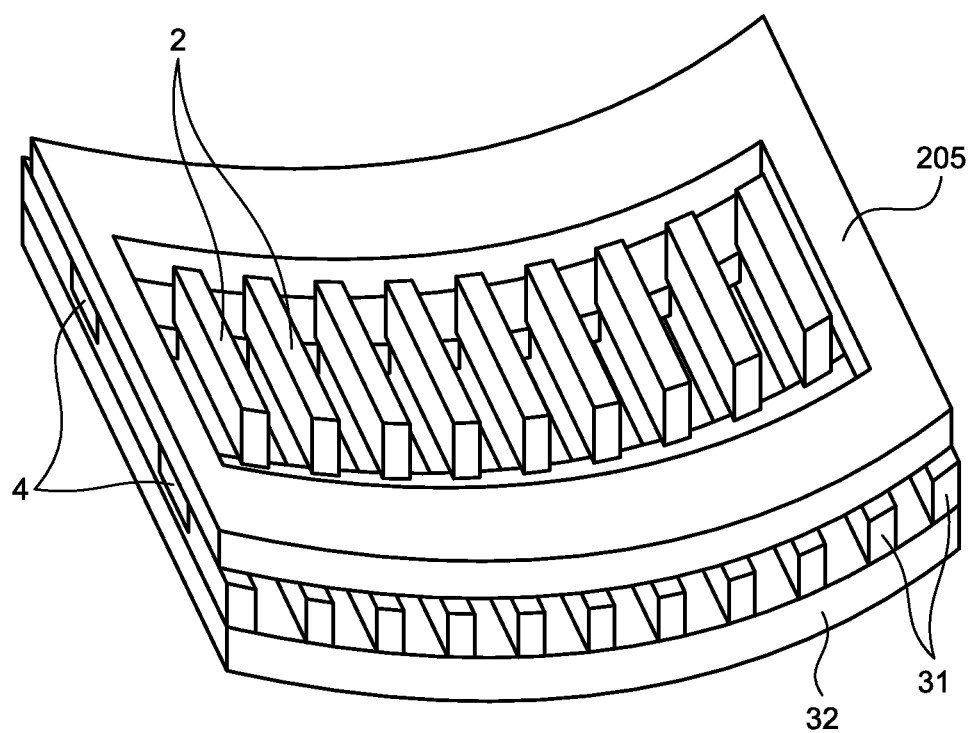
FIG. 8 is a perspective view showing part of an ultrasound probe according to a third embodiment.

FIG. 8 is a perspective view showing part of an ultrasound probe according to a third embodiment. As shown in FIG. 8, the ultrasound probe 1 according to the third embodiment includes a rigid member 205 serving as a deformation preventing member that is arranged on a surface of the acoustic matching layer 3 (the first acoustic-matching layer 31) on a side on which the acoustic matching layer 3 is in contact with the piezoelectric devices 2, in contact with the acoustic matching layer 3 (the first acoustic-matching layer 31), similarly to the first embodiment. Because other components can be the same as the first embodiment, explanation is omitted appropriately.

The rigid member 205 is made from a material having high rigidity, and a high softening point that it is not softened at a high temperature of about 40° C. to 50° C. Specifically, the rigid member 205 is made from ceramic, a super engineering plastic such as Polyether ether ketone (PEEK), or the like.

According to the third embodiment, the rigid member 205 in contact with the first acoustic-matching layer 31 prevents deformation of the first acoustic-matching layer 31 and the second acoustic-matching layer 32.

It can be applied, as the ultrasound probe, to an ultrasound endoscope that includes an ultrasound transducer at a distal end portion. The ultrasound transducer converts an electrical pulse signal received from an ultrasound observation device into an ultrasonic pulse (acoustic pulse) to irradiate to a subject, and converts an ultrasound echo reflected from the subject into an electrical echo signal expressed by voltage change to output. The ultrasound endoscope normally includes an imaging optical system and an imaging device, is inserted into a digestive canal (the esophagus, the stomach, the duodenum, the large intestine) or a respiratory organ (the trachea, the bronchus) of the subject, and is capable of imaging a digestive canal or a respiratory organ.

Moreover, as the ultrasound probe, a thin ultrasound miniature probe without an optical system can be applied. The ultrasound miniature probe is usually inserted into the biliary tract, the biliary duct, the pancreatic duct, the trachea, the bronchus, the urethra, or the ureter, and used to observe the peripheral organs (the pancreas, the lungs, the prostate, the bladder, a lymph node, and the like).

Moreover, as the ultrasound probe, an external ultrasound probe that irradiates ultrasonic waves from a body surface of a subject can be applied. The external ultrasound probe is usually used to observe abdominal organs (the liver, the gallbladder, the bladder), the breast (particularly, mammary glands), and the thyroid.

According to the disclosure, an ultrasound probe and an ultrasound endoscope in which deterioration of performance of the ultrasound probe due to heat are suppressed can be obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasound probe comprising:
a casing;
a plurality of piezoelectric devices arranged inside the casing, each piezoelectric device comprising a piezoelectric material and wires configured to electrically connect the piezoelectric material and a coaxial line;
an acoustic matching layer attached to ultrasound radiation surfaces of the piezoelectric devices;
a shared ground arranged on a surface of the acoustic matching layer, on a side on which the acoustic matching layer is in contact with the piezoelectric devices, to allow at least a part of the shared ground to come in contact with the piezoelectric devices;
a metal material formed separately from the wires and arranged in contact with the surface of the acoustic matching layer to surround an outer periphery of the piezoelectric devices and to be spatially offset and separated from the piezoelectric devices, the metal material providing one or more of rigidity to prevent deformation of the acoustic matching layer and heat transfer from the plurality of piezoelectric devices;
the coaxial line configured to transmit a signal to each of the piezoelectric devices; and
a circuit board arranged on an opposite side to the ultrasound radiation surfaces of the piezoelectric devices, the circuit board being configured to electrically connect the piezoelectric devices and the coaxial line.

2. The ultrasound probe according to claim 1, wherein
the metal material having electric conductivity, and is arranged in contact with the shared ground, and
the coaxial line includes a signal line configured to transmit the signal to each of the piezoelectric devices, and an external conductor that is arranged on an outer periphery of the signal line,
the ultrasound probe further comprising
a heat conduction path configured to transfer heat of the metal material to the external conductor by connecting the metal material and the external conductor with each other.

3. The ultrasound probe according to claim 2, wherein the metal material is made from a shape-memory alloy.

4. The ultrasound probe according to claim 1, wherein the acoustic matching layer and the metal material are curved with an identical curvature.

5. The ultrasound probe according to claim 1, wherein the wires are arranged on each of two sides of the plurality of piezoelectric devices to each contact with the piezoelectric material; and
the metal material is arranged to be spatially offset and separated from the wires.

6. The ultrasound probe according to claim 1, wherein the shared ground is arranged between each piezoelectric device and the acoustic matching layer.

7. The ultrasound probe according to claim 1, wherein the shared ground is embedded in the acoustic matching layer.

8. An ultrasound endoscope comprising:
an imaging optical system to image a subject;
a casing;
a plurality of piezoelectric devices that are arranged inside the casing, each piezoelectric device comprising a piezoelectric material and wires configured to electrically connect the piezoelectric material and a coaxial line;
an acoustic matching layer that is attached to ultrasound radiation surfaces of the piezoelectric devices;
a shared ground that is arranged on a surface of the acoustic matching layer, on a side on which the acoustic matching layer is in contact with the piezoelectric devices, to allow at least a part of the shared ground to come contact with the piezoelectric devices;
a metal material formed separately from the wires and that is arranged in contact with the surface of the acoustic matching layer to surround an outer periphery of the piezoelectric devices and to be spatially offset and separated from the piezoelectric devices, the material providing one or more of rigidity to prevent deformation of the acoustic matching layer and heat transfer from the plurality of piezoelectric devices;
the coaxial line configured to transmit a signal to each of the piezoelectric devices; and
a circuit board that is arranged on an opposite side to the ultrasound radiation surfaces of the piezoelectric devices, the circuit board being configured to electrically connect the piezoelectric devices and the coaxial line.

* * * * *